United States Patent
Board

(10) Patent No.: US 6,679,119 B2
(45) Date of Patent: *Jan. 20, 2004

(54) MULTI-FUNCTION STRESS WAVE SENSOR

(75) Inventor: David B. Board, Boca Raton, FL (US)

(73) Assignee: Swantech, LLC, Fort Lauderdale, FL (US)

( * ) Notice: Subject to any disclaimer, the term of this patent is extended or adjusted under 35 U.S.C. 154(b) by 138 days.

This patent is subject to a terminal disclaimer.

(21) Appl. No.: 09/870,025

(22) Filed: May 30, 2001

(65) Prior Publication Data

US 2002/0043106 A1 Apr. 18, 2002

Related U.S. Application Data

(63) Continuation-in-part of application No. 09/636,697, filed on Aug. 11, 2000.

(51) Int. Cl.[7] ............................ G01N 29/00; G01H 17/00
(52) U.S. Cl. ............................. 73/579; 73/587; 73/599; 73/602; 702/56
(58) Field of Search .................... 73/579, 597, 598, 73/599, 600, 602, 584, 593, 660, 662, 659, 587; 702/56

(56) References Cited

U.S. PATENT DOCUMENTS

| | | | | |
|---|---|---|---|---|
| 3,554,012 A | | 1/1971 | Sohoel | 73/67.2 |
| 3,842,663 A | * | 10/1974 | Harting et al | 73/593 |
| 3,924,456 A | * | 12/1975 | Vahaviolos | 73/770 |
| 4,207,771 A | * | 6/1980 | Carlos et al. | 73/587 |
| 4,429,578 A | | 2/1984 | Darrel et al. | 73/659 |
| 4,530,240 A | | 7/1985 | Board et al. | 73/593 |
| 5,004,985 A | * | 4/1991 | Holroyd et al. | 324/727 |
| 5,005,142 A | | 4/1991 | Lipchak et al. | 364/550 |
| 5,043,736 A | | 8/1991 | Darnell et al. | 342/357 |
| 5,101,162 A | * | 3/1992 | Webster et al. | 324/618 |
| 5,115,671 A | | 5/1992 | Hicho | 73/488 |
| 5,210,704 A | | 5/1993 | Husseiny | 364/551.02 |

(List continued on next page.)

OTHER PUBLICATIONS

Xu et al., "An ANS Based Helicopter Transmission Diagnostic System," IEEE, 8/97.

Yen, "Health Monitoring of Vibration Signatures," IEEE, date unknown—(Since date unknown cited in an abundance of caution).

Yen et al., "Health Monitoring of Vibration Signatures in Rotorcraft Wings," IEEE, date unknown—(Since date unknown cited in an abundance of caution).

Marciano et al., "Mechanical System Condition Monitor (MSCM) System Design," IEEE, 8/97.

*Primary Examiner*—Hezron Williams
*Assistant Examiner*—Jacques Saint-Surin
(74) *Attorney, Agent, or Firm*—Malin, Haley & DiMaggio, P.A.

(57) ABSTRACT

A sensor for detecting stress waves for use in a stress wave analysis system. The stress waves are preferably detected in a narrow frequency range of 35–40 KHz. At this range, stress waves from friction and impact sources typically propagate through machine structures at detectable amplitudes. In order to maximize the signal to noise ratio of stress waves, relative to background noise and vibration, the sensor of the present invention is designed and calibrated with a frequency response and damping features that are specifically tailored for stress wave analysis. The sensor is a multi-functional sensor that can measure a number of logically related parameters for indicting the mechanical condition of a machine. It is often desirable to measure both friction and one or more other parameters appropriate for indication of a machine's health, where all of the measuring capability is contained in one sensor. The multi-functional capability of the present invention significantly reduces the acquisition, installation, and maintenance costs of the condition monitoring instrumentation system.

58 Claims, 10 Drawing Sheets

U.S. PATENT DOCUMENTS

| | | | |
|---|---|---|---|
| 5,239,468 A | 8/1993 | Sewersky et al. | 364/424.03 |
| 5,309,379 A | 5/1994 | Rawlings et al. | 364/578 |
| 5,333,240 A | 7/1994 | Matsumoto et al. | 395/23 |
| 5,365,787 A | 11/1994 | Hernandez et al. | 73/660 |
| RE34,975 E * | 6/1995 | Orban et al. | 367/34 |
| 5,566,092 A | 10/1996 | Wang et al. | 364/551.02 |
| 5,581,016 A * | 12/1996 | Gonzalez et al. | 73/35.06 |
| 5,602,761 A | 2/1997 | Spoerre et al. | 364/554 |
| 5,608,845 A | 3/1997 | Ohtsuka et al. | 395/50 |
| 5,659,136 A * | 8/1997 | Koch et al. | 73/462 |
| 5,734,087 A * | 3/1998 | Yamashita | 73/1.15 |
| 5,852,793 A * | 12/1998 | Board et al. | 702/56 |
| 5,875,420 A | 2/1999 | Piety et al. | 702/182 |
| 5,952,587 A | 9/1999 | Rhodes et al. | 73/862.541 |
| 6,076,405 A | 6/2000 | Schoess | 73/587 |

* cited by examiner

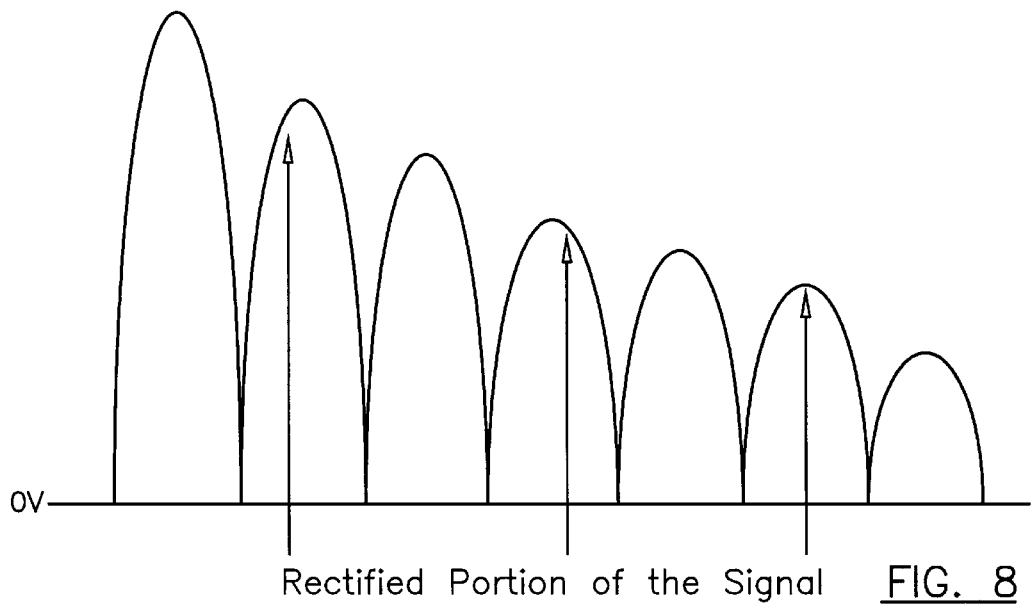
Rectified Portion of the Signal     FIG. 8
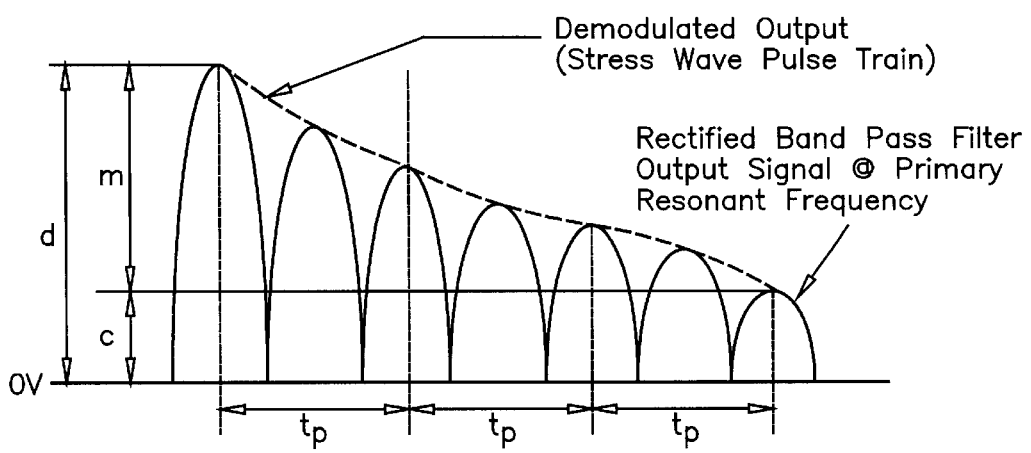
$t_p$ = 1/40000 cps = .000025 seconds
$3t_p$ = .000075 seconds
$5t_p$ = .000125 seconds
$8t_p$ = .0002 seconds
FIG. 9

----------- Stress Wave Pulse Train
m = modulation amplitude
$8t_p$ = 1 cycle of a Stress Wave Pulse Train = 5000 Hz

MULTI-FUNCTION STRESS WAVE SENSOR

This application is a continuation-in-part of Ser. No. 09/636,697, filed Aug. 11, 2000.

BACKGROUND OF THE INVENTION

1. Field of the Invention

The present invention is generally directed to sensors and particularly to multi-functional sensors that can, using stress wave analysis and a number of logically related parameters, indicate the mechanical condition of a machine.

2. Description of Related Art

Stress wave analysis is an ultrasonic instrumentation technique that is used for measurement of friction and shock in mechanical devices. Stress waves are in the form of high frequency structure borne sounds caused by friction between moving parts. The analysis of the stress waves involves the detection and amplification of the high frequency sounds. In addition to the high frequency sounds, other noises and vibration signals are also present, which are not directly related to the stress waves. However, these other signals can interfere with proper analysis of any stress waves emitted by a mechanical device and should be eliminated.

Past attempts at stress wave analysis have incorporated specially selected piezoelectric accelerometers as stress wave sensors. However, these transducers are not specifically designed to detect stress waves, and suffer important shortcomings relative to Analog Signal Conditioning ("ASC") and Digital Signal Processing ("DSP") elements of stress wave analysis instrumentation, such as those shown in FIG. 1.

An accelerometer, when used as a stress wave sensor, is often selected to have maximum repeatability of its primary resonant frequency between 30 Khz and 40 Khz, and its sensitivity at the primary resonant frequency. When secondary resonances are also present in the sensor's frequency response, they are often very difficult, if not impossible, to eliminate, or control, with the same precision as the primary resonance, as shown in FIG. 2. Efforts to adjust or control these secondary resonances may also cause unintended and undesirable changes in the sensitivity of the primary resonance.

In addition to the friction measurements made by stress wave sensors to monitor the mechanical condition or "health" of a machine, it is often desirable to measure both friction and one or more other parameters appropriate for indication of a machine's health, where all of the measuring capability is contained in one sensor. Such multi-function sensors can significantly reduce the acquisition, installation, and maintenance costs of the condition monitoring instrumentation system.

Accordingly, what is needed in the art is a sensor having characteristics that receives stress wave signals while discarding background noises and vibrations, and more particularly, a multi-functional sensor that is capable of detecting stress wave signals and one or more other parameters used to measure and monitor the health of a machine or machine components. It is therefore to the effective resolution of the shortcomings of the prior art that the present invention is directed.

BRIEF SUMMARY OF THE INVENTION

The present invention relates to a sensor having characteristics designed specifically for detecting stress waves for use in a stress wave analysis system. In order to eliminate vibration, audible noise and acoustic emission sources that are not directly related to friction and mechanical impact events in operating machinery, it is preferred to detect stress waves in a narrow frequency range, such as, but not limited to, 35 Khz to 40 KHz. At this frequency range, stress waves from friction and impact sources typically propagate through machine structures at detectable amplitudes. Thus, in order to maximize the signal to noise ratio of stress waves, relative to background noise and vibration, the sensor of the present invention is designed and calibrated with a frequency response and damping characteristics that are specifically tailored for stress wave analysis.

The sensor of the present invention preferably satisfies the following three criteria:

(a) has a resonant gain of approximately 30 db, at its primary resonant frequency, to assure adequate selective amplification of stress waves;

(b) provide a total energy content of the Resonant Energy Integral within a specified tolerance band (i.e. +/−10% of a standard value) and which can be measurable using standard test equipment and fixtures to produce calibration data that is traceable to recognized standards; and (c) have its resonant output decay to half amplitude in five cycles or less, and be down to no more than twenty (20%) percent of the initial response in the number of cycles that correspond to the corner frequency of the demodulator's low pass filter.

In an alternate embodiment, a multi-function sensor is provided which, in addition to detecting and measuring friction via stress wave analysis, also measures one or more other parameters which are most complementary to stress wave measurement, such as vibration, fluid pressure and temperature.

Accordingly, it is an object of the present invention to provide a sensor having a frequency response and damping characteristics specifically designed for stress wave analysis.

It is another object of the present invention to provide a multifunction sensor that is designed to detect stress waves and other logically related parameters that indicate the mechanical condition of machine components.

In accordance with these and other objects which will become apparent hereinafter, the instant invention will now be described with particular reference to the accompanying drawings.

BRIEF DESCRIPTION OF THE SEVERAL VIEWS OF THE DRAWINGS

FIG. 8 is a graph illustrating a rectified band-pass filter output in accordance with the present invention;

FIG. 9 is a graph illustrating a demodulator output in accordance with the present invention;

DETAILED DESCRIPTION OF THE INVENTION

Figure 12:
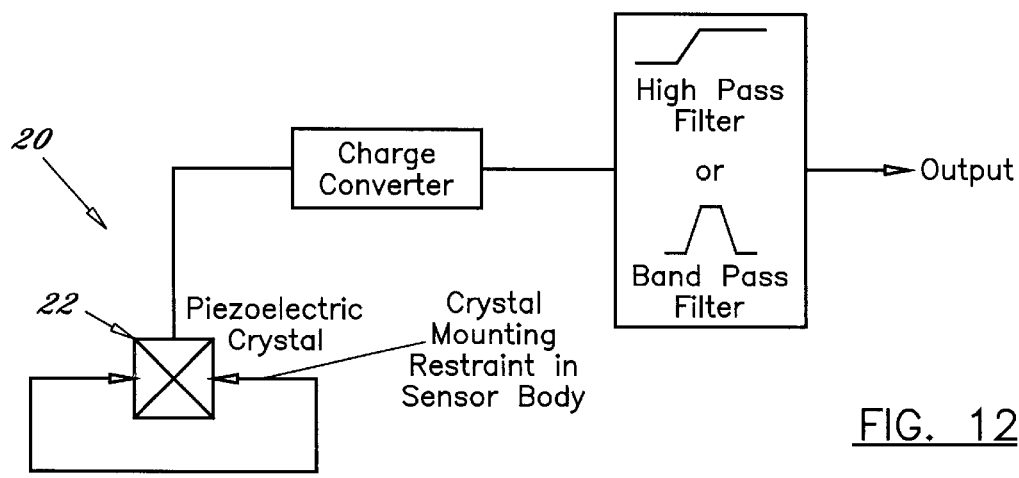
FIG. 12 is a block diagram of one embodiment for the stress wave sensor of the present invention.

The various characteristics of the present invention stress wave sensor are illustrated in the Figures, with FIG. 12 illustrating one embodiment for the components of the stress wave sensor. The stress wave sensor in accordance with the present invention is generally designated as reference numeral 20.

The amplitude of stress waves is relatively small as compared to low frequency sources of vibration and audible sound. As such, it is preferred to selectively amplify signals in a desired frequency range (i.e. 35–40 KHz) which are associated with stress wave signals. The chosen frequency range is preferably well above structural vibration frequencies, which are commonly between 0 to 20 KHz. The chosen frequency range is also preferably within the range of standard test equipment, and below high frequency acoustic emission sources, which are typically occurring at frequencies over 100 KHz.

Though within the scope of the invention, it is not desirable to selectively amplify the stress wave signals electronically, as such techniques also amplify undesired background noise from the noise floor of the electronic circuitry.

Thus, to maximize the stress wave signal to noise ratio of stress wave sensor 20, the transducing element 22 of sensor 20 is designed to have a primary resonant frequency preferably between 35 KHz and 40 KHz. By choosing this preferred frequency range for the resonant response, the desired selective amplification can be accomplished by mechanical means, prior to conversion to an electrical signal which is further processed by ASC and DSP techniques. To assure sufficient selective amplification of the stress wave signals for many common types of machinery, the resonant gain is preferably approximately 30 db. This resonant gain is defined as the ratio of the sensitivity at the primary resonance to the sensitivity at 20 KHz.

Figure 1:
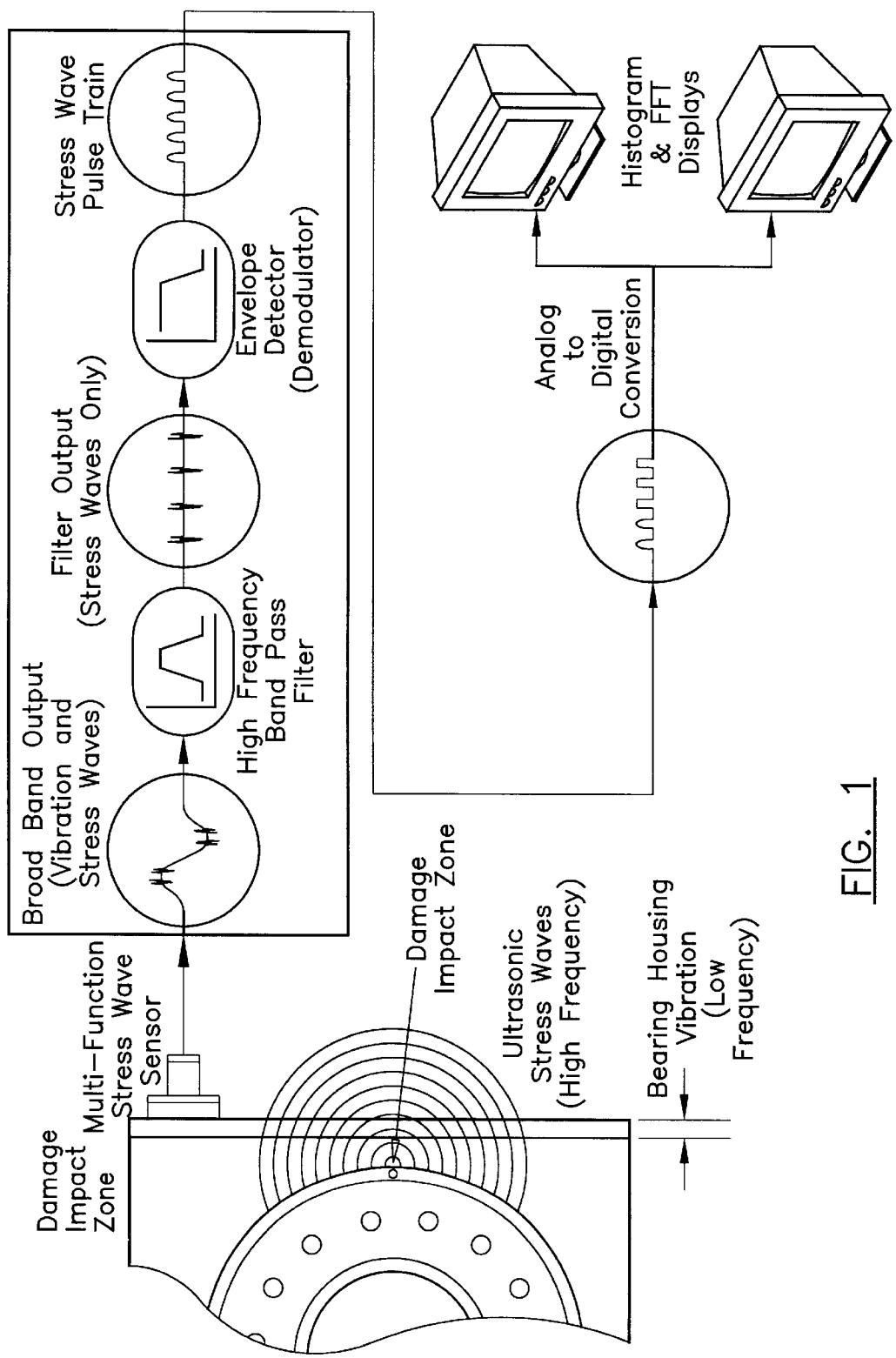
FIG. 1 is a block diagram of a stress wave analysis system including the stress wave sensor of the present invention.
Figure 2:
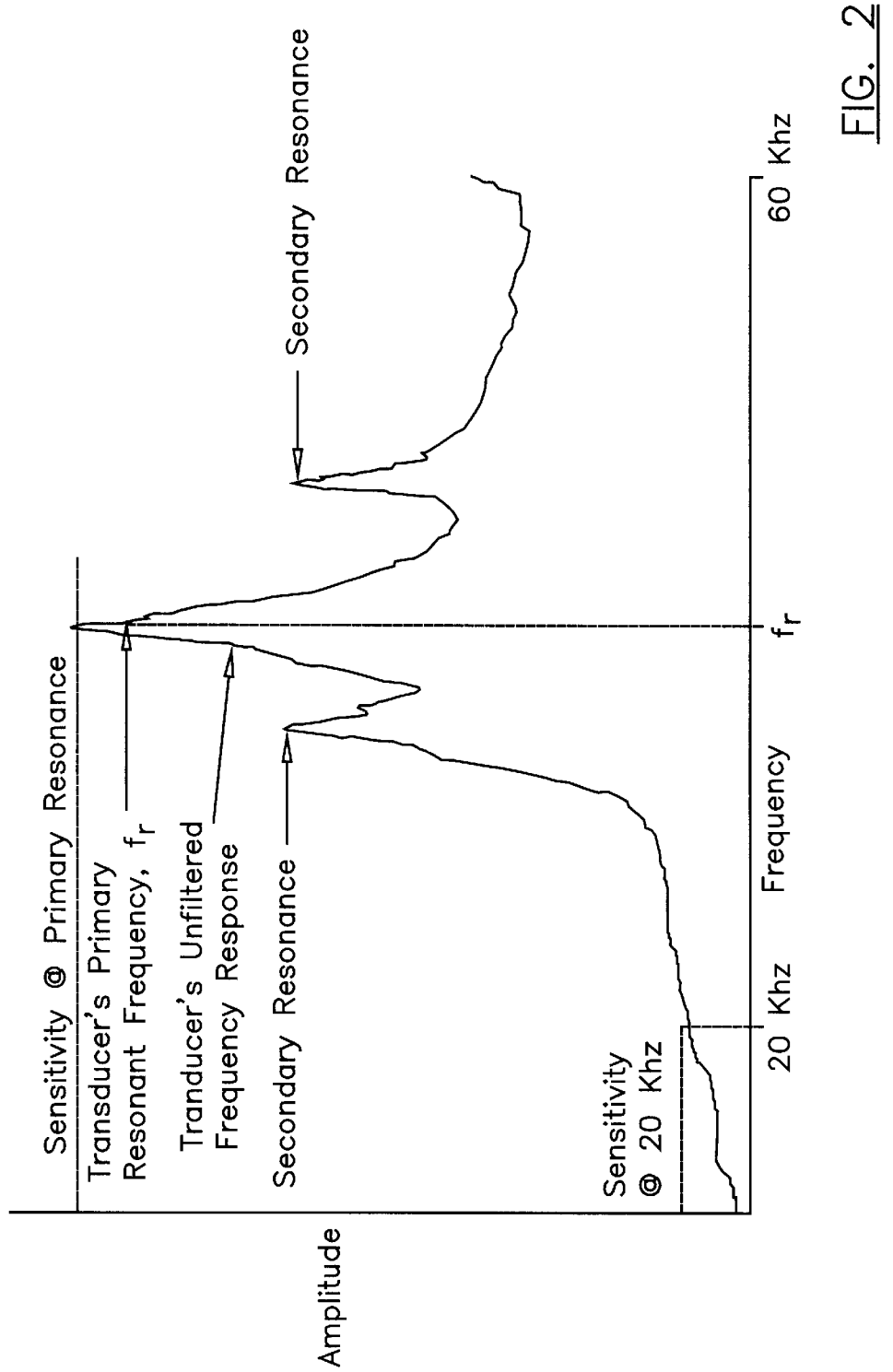
FIG. 2 is a graph illustrating a stress wave sensor frequency response in accordance with the present invention.
Figure 3:
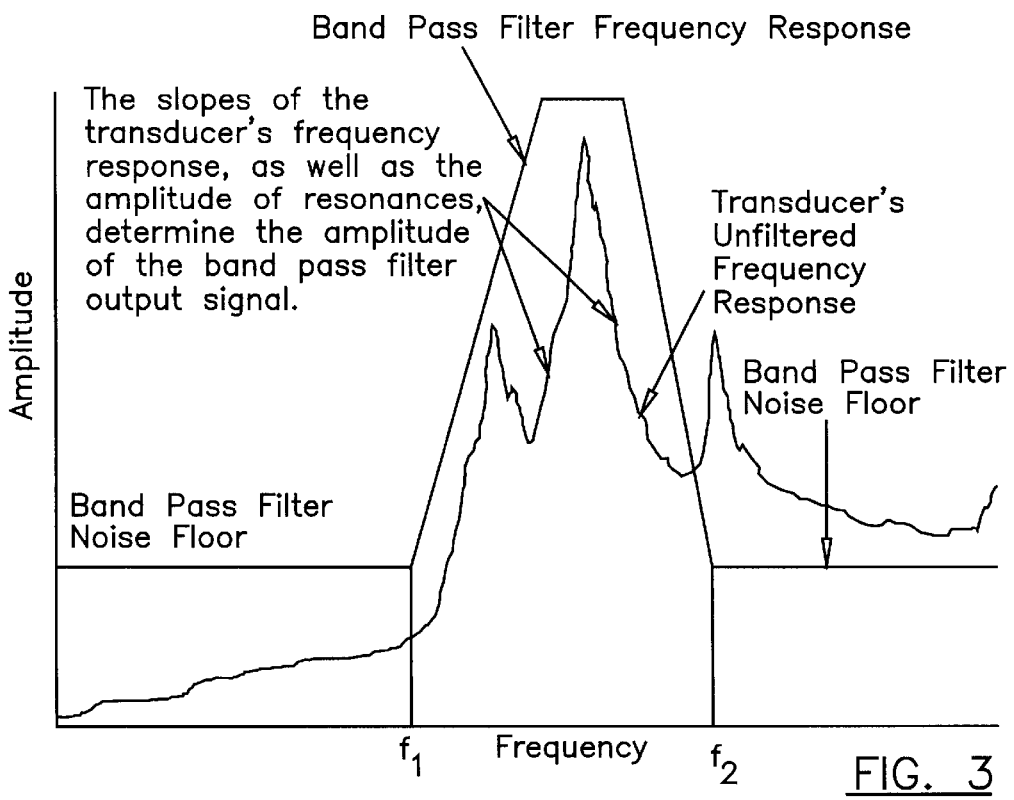
FIG. 3 is a graph illustrating a stress wave sensor frequency response and a band-pass filter response in accordance with the present invention.

As seen in FIG. 3, the secondary resonances which may be present in a sensor's 20 frequency response may fall within the frequency response curve of a band pass filter ("BPF"), and thus can result in undesirable sensor-to-sensor amplitude variations of a filtered and demodulated stress wave pulse train ("SWPT").

Figure 4:
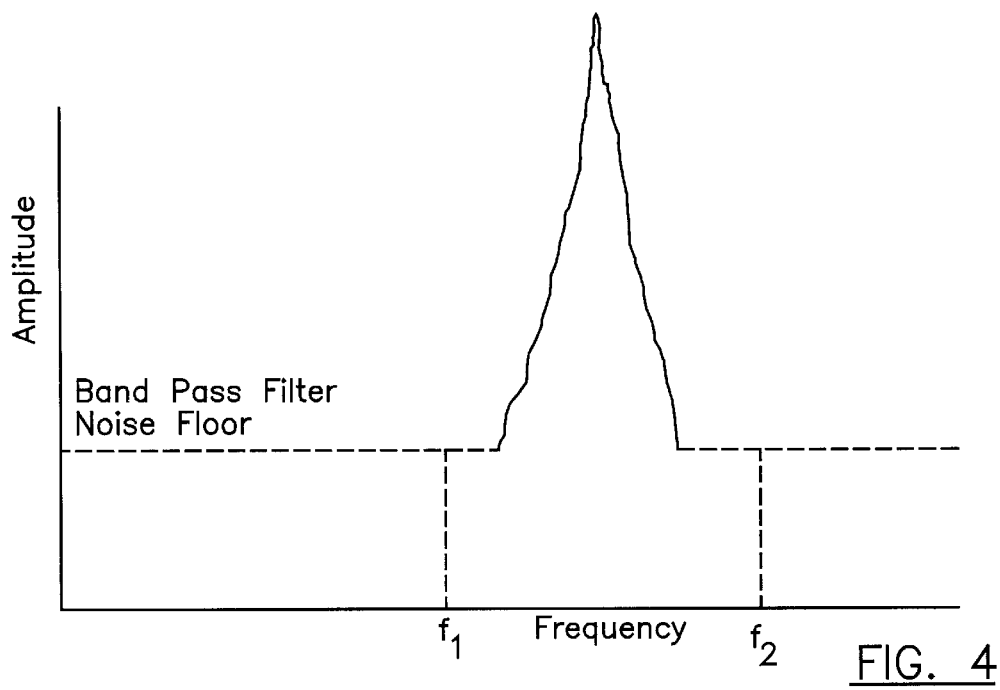
FIG. 4 is a graph illustrating a filtered sensor frequency response in accordance with the present invention.

Another important factor in a stress wave sensor's performance is the overall shape of its frequency response curve. As also seen in FIG. 3, the slopes of the sensor's resonant frequency response, as well as the amplitude of the resonances, determine the amplitude of the BPF's output. The BPF has a relatively flat response between 35 KHz and 40 KHz, and a steep roll-off above and below the pass band, down to the noise floor of the BPF circuitry. From FIG. 3, the frequency where the high pass roll-off intersects the noise floor can be designated $f_1$, and the frequency where the low pass roll-off intersects the noise floor can be designated $f_2$. As seen in FIG. 4, the output of the BPF preferably contains no low frequency signals due to the dynamic response of machine structures (vibration) or audible noise below $f_1$, and no high frequency signals from sources of acoustic emission or secondary resonances at frequencies greater than $f_2$.

Figure 5:
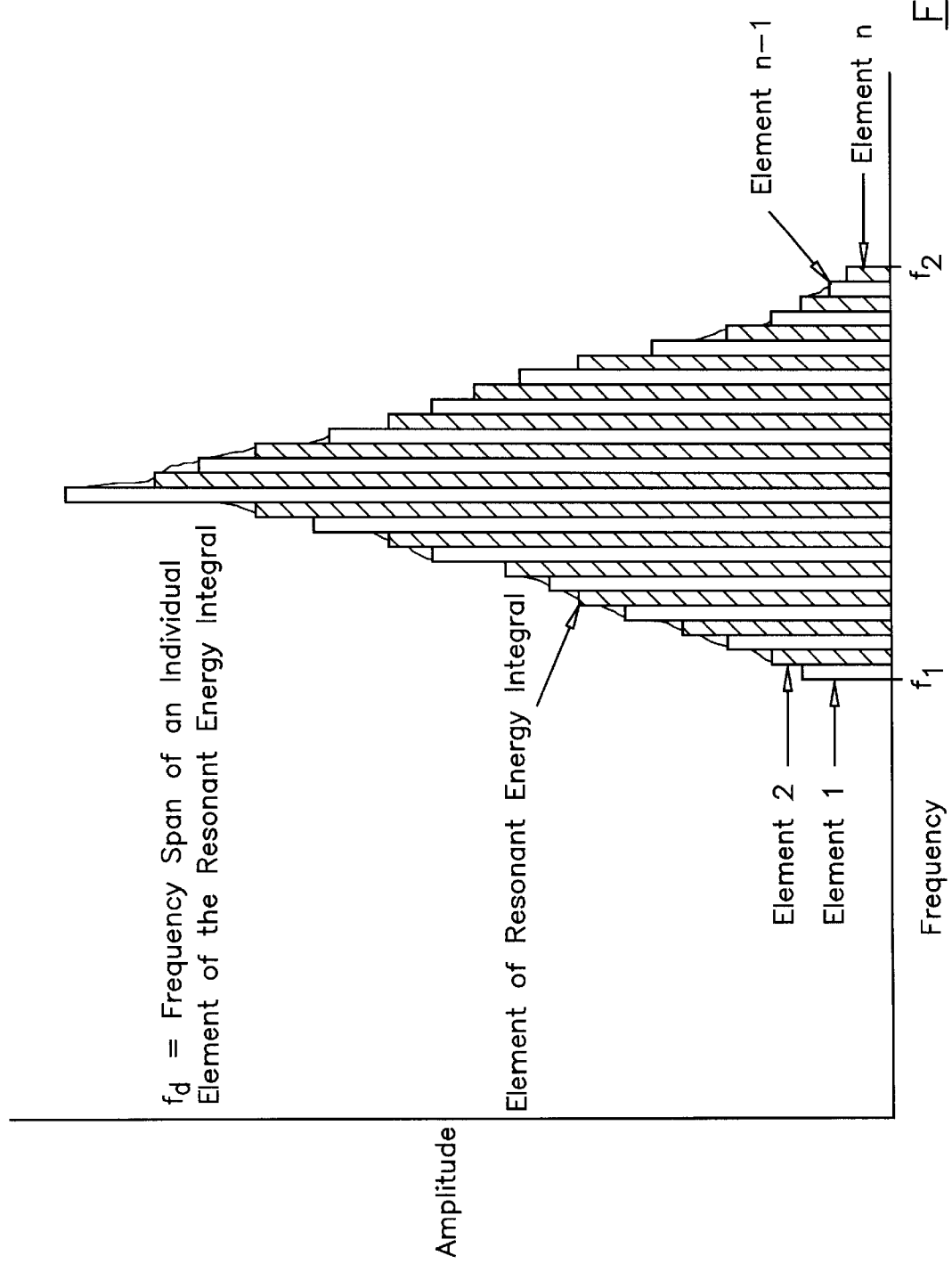
FIG. 5 is a graph illustrating a resonant energy integral in accordance with the present invention.

Preferably, stress wave sensors 20 in accordance with the present invention have sensor-to-sensor repeatability within a specified or predetermined range, which in one embodiment can be plus or minus ten (10%) percent, though such range is not considered limiting and other ranges can be used and are considered within the scope of the invention. Additionally, manufacturing and testing process also preferably produce sensors 20 with calibration data that is traceable to recognized standards, when using standard test equipment and fixtures. Thus, a standard method and stimulating each sensor 20 and measuring its output over the frequency range $f_1$ to $f_2$ is preferably devised and applied by the present invention. For creating a standard method of stimulating each sensor 20, a Resonant Energy Integral (FIG. 5) can be developed.

After assembly, each sensor 20 is preferably placed on a conventional shaker table commonly used by accelerometer manufacturers. The shaker is preferably set at a specified or predetermined frequency and excites a sensor or unit under test ("UUT") by moving sensor 20 up and down at an amplitude that is preferably equal or approximate to a previously determined reference "g" level of acceleration. Sensor's 20 output is measured and preferably recorded as a value "y", which is provided in millivolts per g (mv/g). The excitation frequency of the shaker, is preferably incrementally changed, the amplitude adjusted to achieve the reference "g" level, and another mv/g output value measurement is recorded. This process is repeated at a number ("n"), which can be predetermined, of discrete frequencies over a frequency band ranging from frequency $f_1$ to frequency $f_2$. The repeated process provides the tested sensor's 20 frequency response curve over the frequency band $f_1$ to $f_2$.

Once the frequency response curve is determined, the Resonant Energy Integral can be computed preferably using a multi-step process. This process preferably consists of the following steps:

(1) sensor's 20 sensitivity at each excitation frequency ("$S_n$") is multiplied by an attenuation factor ($A_{bpf}$). The attenuation factor represents the amount of signal attenuation at the particular frequency due to the frequency response of the BPF. The resultant value from the multiplication is the adjusted sensitivity ("$S_{na}$") at frequency $f_n$. In equation form the following step is represented as:

$$S_{na} = (A_{bpf})(S_n)$$

(2) adjusted sensitivity Sna is multiplied by the frequency span ("$f_d$") of the individual element of the Resonant Energy Integral that has $f_n$ at its center. The resultant value from the multiplication is the resonant energy of the nth element of the Resonant Energy Integral. In equation form the following step is represented as:

$$E_{rn} = (S_{na})(f_d)$$

(3) computing the total energy content of the Resonant Energy Integral by summing all of the individual $E_{rn}$ values for elements 1 through n.

This calculated total energy content of the Resonant Energy Integral represents a preferred measure, and most likely best measurement, of the overall signal output from the band pass filter section of the stress wave analysis ASC.

Figure 6:
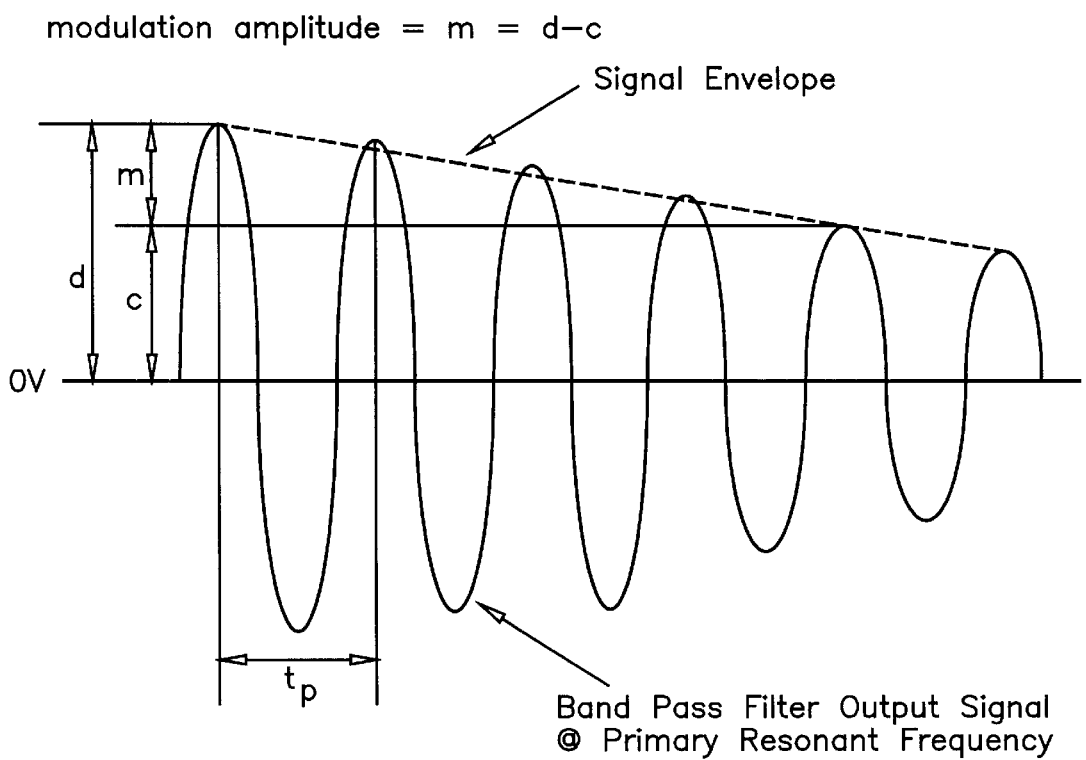
FIG. 6 is a graph illustrating "under damping" of a stress wave signal at its resonant frequency in accordance with the present invention.

As seen in FIG. 6, the band pass filter output is dominated by the primary resonant frequency. FIG. 6 illustrates the time domain response of stress wave sensor's 20 filtered output, due to a single, short duration friction or shock event. The resonant output signal is essentially a damped sign wave that preferably begins at a near zero peak to peak ("p-p") amplitude. When stress waves caused by a high amplitude friction event reach sensor 20, sensor 20 is excited to a zero to peak ("0-p") amplitude of value "d". After a sufficient number of cycles, sensor's 20 amplitude decays back down to its original near zero p-p amplitude. The period of one complete cycle "$t_p$", is the reciprocal of the primary resonant frequency $f_r$. Where the primary resonant frequency is 40 KHz, the following period is calculated as:

$$T_p = 1/f_r = 1/40,000 \text{ cycles/sec} = 0.000025 \text{ sec.}$$

Figure 7:
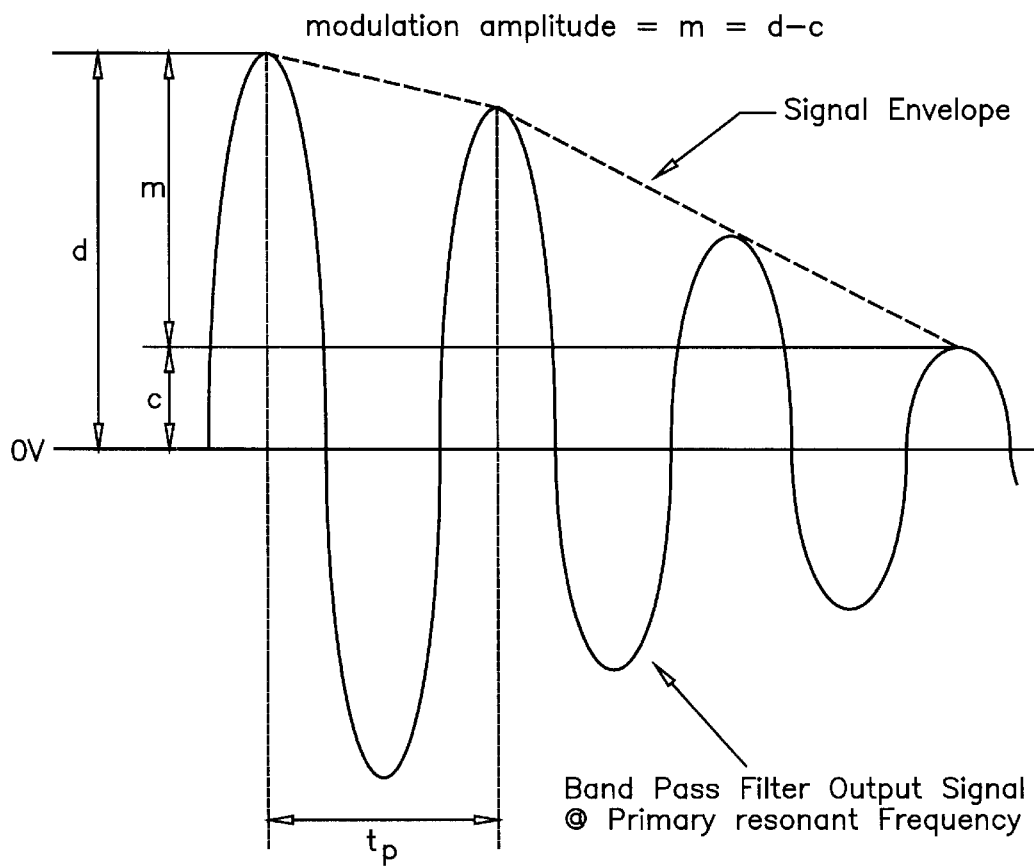
FIG. 7 is a graph illustrating "proper damping" of a stress wave signal at its resonant frequency in accordance with the present invention.

Stress wave analysis depends upon the modulation of sensor's 20 resonant response. Thus, the damping of sensor 20 is preferred in the modulation amplitude at the frequency that can be obtained at the output of the ASC. The modulation amplitude "m" is defined as the amount of signal decay after a certain number of cycles, such as, but not limited, five cycles, following the initial excitation. As also seen in FIG. 6, after the certain number of cycles (i.e. 5), modulation amplitude "m" is less than fifty (50%) percent of the original excitation amplitude "d". This small amount of modulation is preferably undesirable for the detection of multiple friction events and the accurate measurement of their energy content. As such, the sensor 20 response shown in FIG. 6 is considered "under damped". A properly damped response in accordance with the present invention is illustrated in FIG. 7. The response is taken from a sensor 20 preferably with the same resonant frequency. FIG. 7 illustrates specifying damping at the resonant frequency, in addition to the Resonant Energy Integral. By damping relatively quickly (FIG. 7), additional shock and friction events will again modulate the signal.

Figure 10:
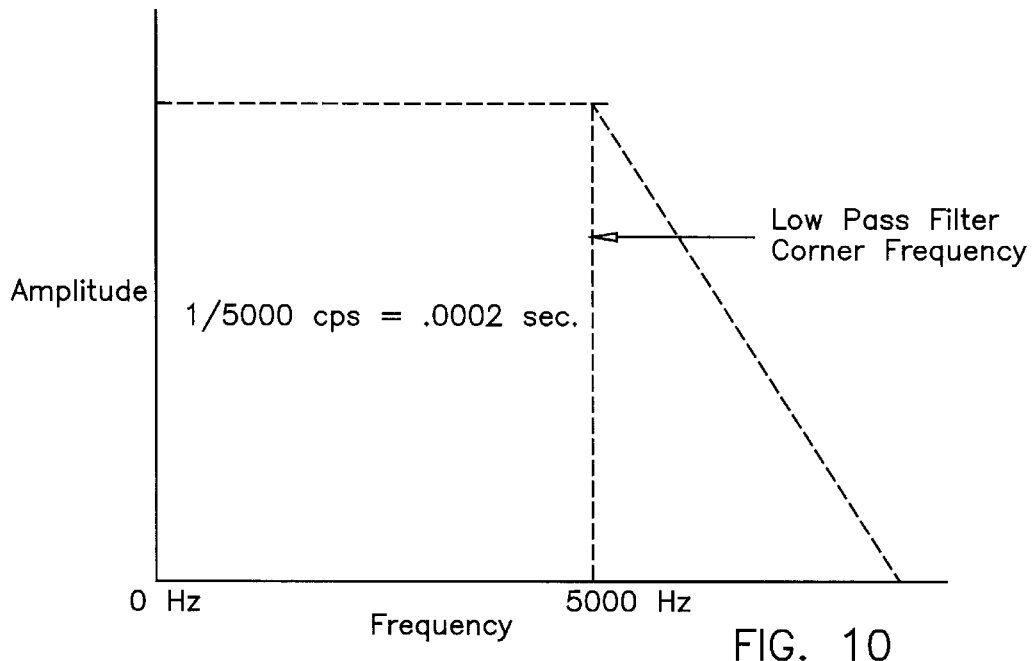
FIG. 10 is a graph illustrating a demodulator low-pass filter frequency response in accordance with the present invention.

FIGS. 8 and 9 illustrate the steps preferably involved in the demodulation portion of the stress wave analysis signal conditioning process. The damped sinusoidal output of the band pass filter is full wave rectified (FIG. 8), preferably prior to low pass filtering. The stress wave pulse train is defined as the demodulated output signal from the low pass filter (FIG. 9). The stress wave pulse train preferably has a frequency content from 0 Hz to the corner frequency of the low pass filter portion of the demodulation circuitry (See FIG. 10).

Sensor 20 can be used in monitoring many different applications (i.e. various shock and friction events from slow speed gear boxes to turbo machinery, etc.), such that its resonant output preferably decays to half amplitude in a specific number of cycles or less. The preferred number of cycles for decaying to half amplitude is five, though such number is not considering limiting and other numbers can be chosen and are considered within the scope of the invention. Furthermore, sensor's 20 resonant output preferably is not more than twenty (20%) percent, or some other determined value, of the initial response "d" in the number of cycles that occur during the time period that corresponds to the corner frequency of the low pass filter.

Figure 11:
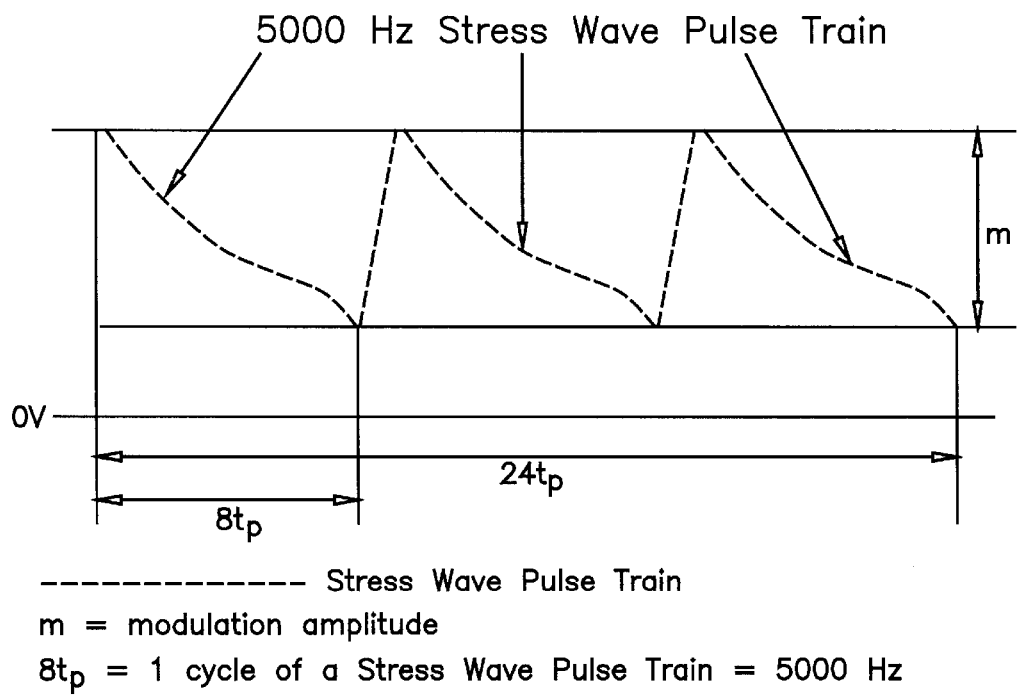
FIG. 11 is a graph illustrating a multiple event demodulator output in accordance with the present invention.

As an example, where a sensor 20 has a primary resonance of 40 KHz, the stress wave signal is preferably damped to less than twenty (20%) percent of its initial amplitude in eight (8) cycles. FIG. 11 illustrates a stress wave pulse train for the example, where the friction source excites sensor 20 at a periodic rate of five thousand (5000) times per second.

FIG. 12 illustrates the major components of one embodiment for a sensor 20 in accordance with the present invention. However other components can be used and are considered within the scope of the invention.

Accordingly, with the present invention the design of stress wave sensor 20 is preferably intimately related to the analog signal conditioning employed to extract the stress wave pulse train signal from broadband sources of excitation that contain in addition to the desired friction and shock events, vibration, audible noise and high frequency acoustic emissions. Sensor's 20 design can also be a function of available calibration test equipment. The transducing element 22 of sensor can be a piezoelectric crystal, or can be based upon Micro Electrical Mechanical Systems (MEMS) technology, or other transducer technology. Sensor 20 preferably satisfies the following three criteria:

(a) has a resonant gain of approximately 30 db, at its primary resonant frequency, to assure adequate selective amplification of stress waves;

(b) provide a total energy content of the Resonant Energy Integral within a specified tolerance band (i.e. +/−10% of a standard value) and which can be measurable using standard test equipment and fixtures to produce calibration data that is traceable to recognized standards; and (c) have its resonant output decay to half amplitude in five cycles or less, and be down to no more than twenty (20%) percent of the initial response in the number of cycles that correspond to the corner frequency of the low pass filter.

Stress wave sensors 20 communicate with an electronic assembly, which processes the stress wave signal(s) received from sensor(s) 20. The electronic assembly is in communication with sensors 20 via conventional cabling. In lieu of conventional cabling, the sensors can communicate with the electronics through wireless technology.

In one embodiment, sensor 20 can include amplification, band pass filtering and demodulation of the stress wave signal at the sensing element. Alternatively, a non-amplified sensor 20 can also be used, preferably with the use of greater stress wave signal amplification outside the sensing element and a lower noise floor than the preferred amplifying and filtering sensor. Preferably, the stress wave frequency of interest ranges from 20 KHz up. However, other values and ranges can be used and/or analyzed and all are considered within the scope of the invention. To reduce the stress wave signal amplitude range and the signal conditioning electronics' sensitivity sensor 20 may incorporate two features: gain and band pass filtering.

Sensor 20 is suitable for use in many applications that require the detection of an impact event within operating machinery, and all of such applications are considered within the scope of the invention.

In an alternate embodiment, sensor 20 is a multi-functional sensor capable of measuring friction as well as additional, logically related parameters, to more accurately determine the mechanical health of a machine.

The additional parameter that is most complementary to stress wave measurement for most condition monitoring applications is vibration. Whether vibration is measured as a displacement, a velocity, or an acceleration, it can be measured with the same transducing element that is used to convert stress waves into electrical signals.

Figure 13:
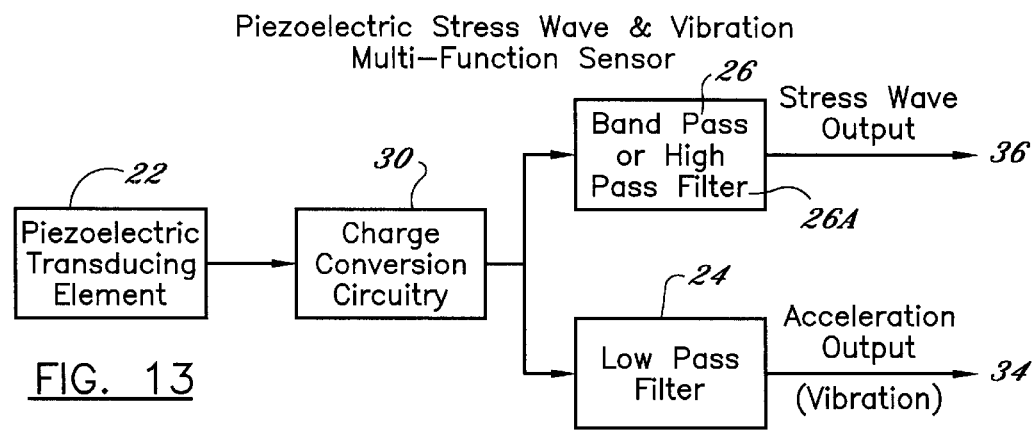
FIG. 13 is a block diagram illustrating a multi-function output utilizing a piezoelectric transducing element in accordance with the present invention.

Referring to FIG. 13, a block diagram illustrating the piezoelectric stress wave and vibration multi-function sensor of the present invention is shown. If transducing element 22 is a piezoelectric crystal, the preferred method of obtaining both vibration and stress wave data from the same sensor is to pass the vibration frequencies by low pass filtering the transducer's electrical output via step 24 and to pass the high frequency resonant response to detect stress waves by parallel band pass filtering the transducer's electrical output via step 26.

The dual function stress wave and vibration sensor 20 of the present invention therefore includes a transducing element 22 with a nearly constant sensitivity to acceleration from a few Hz to several thousand Hz, charge conversion circuitry 30 to convert the charge on the piezoelectric crystal to a time varying voltage waveform, and two parallel filter networks; a Low Pass Filter 24 to pass the vibration frequencies 34, and a Band Pass Filter 26 to pass the stress wave frequencies 36, centered on the crystal's resonant frequency.

The sensor's acceleration output is integrated once for velocity, or twice for a displacement output. In an alternate embodiment, a High Pass Filter 26A replaces the Band Pass Filter 26 to pass the resonant response to the high frequency stress waves. To minimize sensor cost, size and weight, an alternate packaging configuration would move Band Pass Filter 26 or High Pass Filter 26A out of the sensor and include it in the electronic assembly that scans multiple sensors as inputs.

Figure 14:
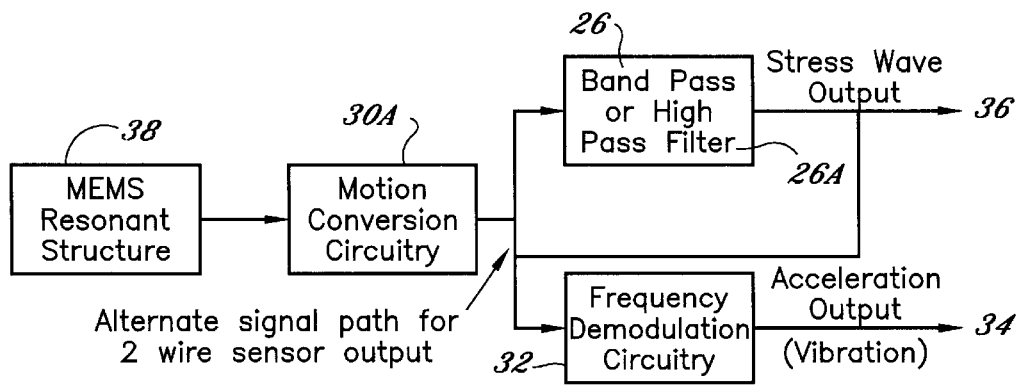
FIG. 14 is a block diagram illustrating a multi-function output utilizing a microelectromechanical resonant structure in accordance with the present invention.

If transducing element 22 is a micro electrical mechanical system (MEMS) device 38, as shown in FIG. 14, the MEMS device is designed having a high Q, high frequency resonance, and about a 30 db sensitivity increase in a narrow frequency band between 25 KHz and 45 KHz. MEMS device 38 can also be mounted inside the sensor's body in such a fashion that acceleration induced forces along the sensor's principle axis will cause a shift in the resonant frequency that is a nearly linear function of the acceleration of the sensor body along its principal axis.

In the embodiment depicted in the block diagram of FIG. 14, both the stress wave data 36 and vibration data 34 are available on a single time domain waveform that can be carried on a single conductor. Motion Conversion Circuitry 30A converts motion detected by MEMS device 38 and converts it to a varying voltage waveform. The amplitude modulation of this waveform's resonant frequency contains stress wave signal 36, and the frequency modulation of the resonant frequency contains vibration signal 34. Thus the vibration signal can be extracted by frequency demodulation via step 32, and the stress wave signal can be extracted using band pass or high pass filtering (via steps 26 or 26A, respectively) at the transducer's resonant frequency. The sensor's acceleration output 34 can be integrated once for a velocity, or twice for a displacement output. To minimize sensor cost, size and weight, alternate packaging configuration moves band pass filter 26 and frequency demodulation circuitry 32 out of sensor 20 and includes them in the electronic assembly that scans multiple sensors as inputs.

Figure 15:
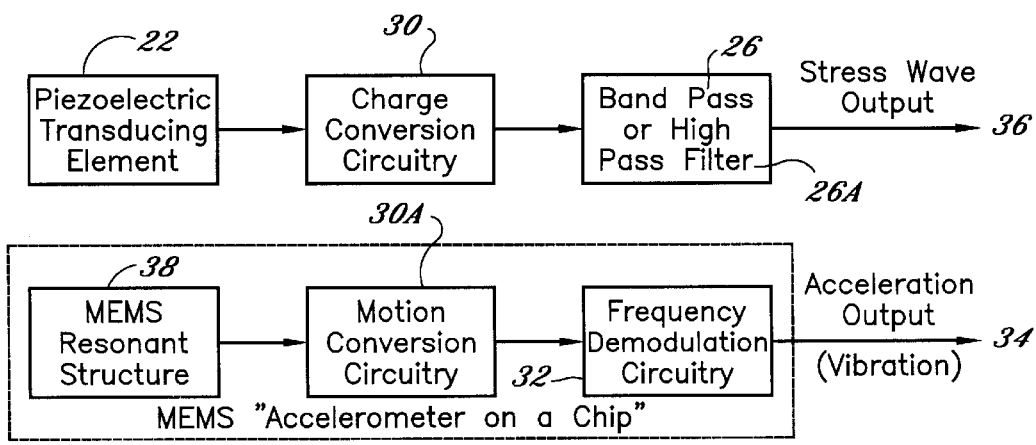
FIG. 15 is a block diagram illustrating a multi-function output utilizing a hybrid piezoelectric transducing element and microelectromechanical resonant structure in accordance with the present invention.

In yet a further embodiment, the existing piezoelectric crystal-based stress wave sensor is modified by the addition of an existing MEMS "accelerometer on a chip" type of circuit. This is shown in FIG. 15. MEMS accelerometers of this nature are commercially available and are small enough to be mounted within the stress wave sensor body in similar fashion to the existing piezoelectric charge converter and filter Integrated Circuit chip. This Piezo-MEMS Hybrid design could have a 2-pin shielded connector, share power and the stress wave signal on one pin, put the MEMS accelerometer output on the other pin, and use the sensor case/cable shield as ground.

The "Hybrid Sensor" described above is a low risk and economical approach to combine stress wave sensing with other physical parameters useful in the measurement of a machine's condition. Examples of this would be the integration of parallel sensing and signal conditioning into a common sensor housing for the following parameters:

Stress waves and Fluid Pressure;
Stress waves and Temperature;
Stress waves, Fluid Pressure and Temperature;
Stress Waves, Vibration and Fluid Pressure;
Stress Waves, Vibration and Temperature; and
Stress Waves, Vibration, Fluid Pressure and Temperature.
Stress Waves, Proximity of Moving Machine Elements It is within the sprit of the present invention to include not only those parameters listed above, but all parameters having logically complementary characteristics, are technically feasible and will be cost effective.

For sensors with two or more functions, it becomes increasingly impractical to have separate conductors in the sensor cable for each measured parameter. Since the multi-functional sensors of the present invention digitize their measurements, the multiple parameters can be formatted so that they appear sequentially in the overall digital data stream sent over the single conductor to the monitoring device. Since some sensors will be also capable of operating in different modes under command from the monitoring device, it is feasible to tell the multi-function sensor what parameters are required, at what measurement interval they should be acquired and in what order they should be sent back to the monitoring device. These data acquisition sequences can also be dynamically varied as a function of the analysis performed by the monitoring device.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A multi-function stress wave sensor for detecting, measuring and processing logically complementary input parameter signals indicative of a machine's health, in communication with an electronic assembly, said sensor comprising:

a transducing element generating a primary resonant frequency;

energy conversion circuitry in communication with said transducing element; and a plurality of filter networks in communication with said energy conversion circuitry, said plurality of filter networks attenuating certain frequencies of said signals, wherein said sensor has a resonant gain at its primary resonant frequency to allow for selective amplification of stress waves received from friction and mechanical impacts;

wherein said plurality of filter networks includes a band or high pass filter and a low pass filter;

wherein said sensor has a resonant output of a specific amplitude, said resonant output decaying to half amplitude by a predetermined number of cycles.

2. The stress wave sensor of claim 1 wherein said predetermined number of cycles is five.

3. The stress wave sensor of claim 1 wherein said resonant output has a peak amplitude of a certain initial value which is reduced to not more than approximately twenty percent of the initial value in a number of cycles that occur during a time period corresponding to a corner frequency of a demodulator low pass filter in said electronic assembly.

4. The multi-function stress wave sensor of claim 1 wherein a cutoff frequency for attenuation by the low pass filter, for a complementary input parameter, is approximately 20 KHz.

5. The stress wave sensor of claim 1 wherein said primary resonant frequency is above a natural vibration frequency of a monitored device.

6. The stress wave sensor of claim 1 wherein said transducing element is a piezoelectric crystal.

7. The stress wave sensor of claim 6 further including a body member wherein said piezoelectric crystal is mounted within said body member by at least one restraint member.

8. The stress wave sensor of claim 7 wherein said energy conversion circuitry, said high pass or band pass filter and said low pass filter are also disposed within said body member.

9. The stress wave sensor of claim 8 further comprising a micro electrical mechanical system circuit disposed within said body member.

10. The stress wave sensor of claim 1 wherein said transducing element is a micro electrical mechanical system.

11. The stress wave sensor of claim 10 further including a body member wherein said micro electrical mechanical system is mounted within said body member by at least one restraint member.

12. The stress wave sensor of claim 1 wherein said low pass filter allows for passage of vibration frequencies and said high pass or band pass filter allows for passage of stress wave frequencies.

13. The stress wave sensor of claim 1 wherein said logically complementary input parameter signals are stress waves and fluid pressure.

14. The stress wave sensor of claim 1 wherein said logically complementary input parameter signals are stress waves and temperature.

15. The stress wave sensor of claim 1 wherein said logically complementary input parameter signals are stress waves, fluid pressure and temperature.

16. The stress wave sensor of claim 1 wherein said logically complementary input parameter signals are stress waves, vibration and fluid pressure.

17. The stress wave sensor of claim 1 wherein said logically complementary input parameter signals are stress waves, vibration and temperature.

18. The stress wave sensor of claim 1 wherein said logically complementary input parameter signals are stress waves, vibration, fluid pressure and temperature.

19. The stress wave sensor of claim 1 wherein said logically complementary input parameter signals are stress waves and proximity of rotating machine elements.

20. The stress wave sensor of claim 1 wherein said sensor has a resonant gain of approximately 30 db at its primary resonant frequency to allow for selective amplification of stress waves received from mechanical impacts.

21. The stress wave sensor of claim 1 wherein said low pass filter attenuates signals above a first selected frequency and said band pass filter attenuates received signals which are outside a selected frequency range.

22. The stress wave sensor of claim 21 wherein an upper frequency for the selected frequency range is approximately 125% of a primary resonant frequency of said transducing element.

23. The stress wave sensor of claim 1 wherein said logically complementary input parameter signals are available in a single time domain waveform that is parallel processed by the plurality of filter networks to respective low frequency and high frequency signals on separate conductors.

24. The stress wave sensor of claim 1 wherein the primary resonant frequency is higher than a cutoff frequency for the high pass filter.

25. The stress wave sensor of claim 1 wherein the primary resonant frequency is approximately at a center of frequencies for the band pass filter.

26. The stress wave sensor of claim 1 wherein a pass band of the band pass filter is approximately twice as wide as a corner frequency of a demodulator low pass filter in the electronic assembly.

27. The multi-function sensor of claim 1 wherein attenuation of certain frequencies by said high pass or band pass filter helps to prevent saturation of any signal conditioning amplification outside of the sensor.

28. A multi-function stress wave sensor for detecting, measuring and processing logically complementary input parameter signals indicative of a machine's health, in communication with an electronic assembly, said sensor comprising:

a transducing element generating a primary resonant frequency;

energy conversion circuitry in communication with said transducing element; and a plurality of filter networks in communication with said energy conversion circuitry, said plurality of filter networks attenuating certain frequencies of said signals, wherein said sensor has a resonant gain at its primary resonant frequency to allow for selective amplification of stress waves received from friction and mechanical impacts;

wherein said logically complementary input parameter signals are available in a single time domain waveform that is transmitted sequentially in a single data stream on a single conductor from said sensor to said electronic assembly.

29. A multi-function stress wave sensor for detecting, measuring and processing logically complementary input parameter signals indicative of a machine's health, in communication with an electronic assembly, said sensor comprising:

a transducing element generating a primary resonant frequency;

energy conversion circuitry in communication with said transducing element; and a plurality of filter networks in communication with said energy conversion circuitry, said plurality of filter networks attenuating certain frequencies of said signals, wherein said sensor has a resonant gain at its primary resonant frequency to allow for selective amplification of stress waves received from friction and mechanical impacts;

wherein the electronic assembly further comprises data acquisition means for instructing the sensor which said input parameters are required, at what time interval each said input parameters are to be acquired at, and in what sequential order said input parameters are to be sent back to the electronic assembly.

30. A multi-function stress wave system for detecting, measuring and processing logically complementary input parameter signals indicative of a machine's health, said system comprising:
  a sensor including a transducing element generating a primary resonant frequency approximately between 35 KHz to 40 KHz and energy conversion circuitry in communication with said transducing element, said sensor having a resonant gain of approximately 30 db at its primary resonant frequency to allow for selective amplification of stress waves, said sensor having a resonant output of a specific amplitude, said resonant output decaying to half amplitude by a predetermined number of cycles; and
  an electronic assembly including a plurality of filter networks in communication with said energy conversion circuitry for attenuating received signals that fall below a selected frequency of approximately 20 KHz.

31. The stress wave system of claim 30 wherein said plurality of filter networks include a vibration low pass filter and a stress wave band pass filter.

32. The stress wave system of claim 30 wherein said predetermined number of cycles is five.

33. The stress wave system of claim 31 wherein said resonant output has a peak amplitude of a certain initial value which is reduced to not more than approximately twenty percent of the initial value in a number of cycles that occur during a time period corresponding to a corner frequency of a demodulator low pass filter in the electronic assembly.

34. The stress wave system of claim 30 wherein said transducing element is a piezoelectric crystal.

35. The stress wave system of claim 34 further including a body member situated within said sensor wherein said piezoelectric crystal is mounted within said body member by at least one restraint member.

36. The stress wave system of claim 30 wherein said energy conversion circuitry and said plurality of filters are also disposed within said body member.

37. The stress wave system of claim 36 further comprising a micro electrical mechanical system circuit disposed within said body member.

38. The stress wave system of claim 30 wherein said transducing element is a micro electrical mechanical system.

39. The stress wave system claim 38 further including a body member wherein said micro electrical mechanical system is mounted within said body member by at least one restraint member.

40. The stress wave system of claim 37 wherein one of said logically complementary input parameter signals is vibration, said vibration low pass filter allows for passage of vibration frequencies and said band pass filter allows for passage of stress wave frequencies.

41. The stress wave system of claim 30 wherein said filter networks comprise a low pass filter to allow for passage of vibration frequencies and a high pass filter to allow for passage of stress wave frequencies.

42. The stress wave system of claim 30 wherein said logically complementary input parameter signals are stress waves and fluid pressure.

43. The stress wave system of claim 30 wherein said logically complementary input parameter signals are stress waves and temperature.

44. The stress wave system of claim 30 wherein said logically complementary input parameter signals are stress waves, fluid pressure and temperature.

45. The stress wave system of claim 30 wherein said logically complementary input parameter signals are stress waves, vibration and fluid pressure.

46. The stress wave system of claim 30 wherein said logically complementary input parameter signals are stress waves, vibration and temperature.

47. The stress wave system of claim 30 wherein said logically complementary input parameter signals are Stress waves, vibration, fluid pressure and temperature.

48. The stress wave system of claim 30 wherein said logically complementary input parameter signals are stress waves and proximity of moving machine elements.

49. The stress wave system of claim 30 wherein said logically complementary input parameter signals are available in a single time domain waveform that can be transmitted sequentially in a single data stream on a single conductor from said sensor to said electronic assembly.

50. The stress wave sensor of claim 30 wherein the electronic assembly further comprises data acquisition means for instructing the sensor which said input parameters are required, at what time interval each said input parameters are to be acquired at, and in what sequential order said input parameters are to be sent back to the electronic assembly.

51. A multi-function stress wave sensor for detecting, measuring and processing logically complementary input parameter signals indicative of a machine's health, in communication with an electronic assembly, said sensor comprising:
  a transducing element generating a primary resonant frequency;
  energy conversion circuitry in communication with said transducing element; and
  a plurality of filter networks in communication with said energy conversion circuitry for attenuating certain frequencies of said signals prior to any external amplification or signal conditioning of said signals;
  wherein said logically complementary input parameter signals are available in a single time domain waveform that is parallel processed by the plurality of filter networks to respective low frequency and high frequency signals on separate conductors.

52. A sensor for detecting, measuring and processing logically complementary input parameter signals indicative of a machine's health, in communication with an electronic assembly, said sensor comprising:
  a transducing element generating a primary resonant frequency;
  motion conversion circuitry in communication with said transducing element for converting motion detected by said transducing element into a varying voltage waveform;
  a high pass or band pass filter network in communication with said motion conversion circuitry for extracting a stress wave signal at the primary resonant frequency prior to any external signal conditioning; and
  frequency demodulation circuitry in communication with said motion conversion circuitry for extracting a vibration signal at the primary resonant.

53. The sensor of claim 52 wherein said transducing element is a micro electrical mechanical system.

54. A sensor for detecting, measuring and processing logically complementary input parameter signals indicative of a machine's health, in communication with an electronic assembly, said sensor comprising:

a first transducing element generating a first primary resonant frequency;

a second transducing element generating a second primary resonant frequency;

energy conversion circuitry in communication with said first transducing element;

motion conversion circuitry in communication with said second transducing element for converting motion detected by said second transducing element into a varying voltage waveform;

a high pass or band pass filter network in communication with said energy conversion circuitry for attenuating certain frequencies of said signals prior to any external signal conditioning; and frequency demodulation circuitry in communication with said motion conversion circuitry for extracting a vibration signal at the second primary resonant frequency.

55. The sensor of claim 54 wherein said high pass or band pass filter network extracting a stress wave signal at the first primary resonant frequency prior to any external signal conditioning.

56. The sensor of claim 54 wherein said first transducing element is a piezoelectric crystal.

57. The sensor of claim 54 wherein said second transducing element is a micro electrical mechanical system.

58. A multi-function stress wave sensor for detecting, measuring and processing logically complementary input parameter signals indicative of a machine's health, in communication with a remote electronic assembly, said sensor comprising:

a transducing element generating a primary resonant frequency;

energy conversion circuitry in communication with said transducing element;

other logically complementary input parameter circuitry in communication with said transducing element;

a high pass or band pass filter in communication with said energy conversion circuitry for attenuating certain frequencies of said signals prior to any amplification of said signals; and a low pass filter in communication with said other logically complementary input parameter circuitry;

wherein the input parameter signals includes a low frequency component and a high frequency component; wherein said high pass or band pass filter attenuates said low frequency component so that the high frequency component represents a significant percentage of the filtered signal prior to any subsequent amplification outside of the sensor.

* * * * *